US00PP13247P2

(12) United States Plant Patent
Shimizu

(10) Patent No.: US PP13,247 P2
(45) Date of Patent: Nov. 19, 2002

(54) *HYDRANGEA ANOMALA* **SUBSPECIES *PETIOLARIS* PLANT NAMED 'KUGA VARIEGATED'**

(75) Inventor: Toshiro Shimizu, Yamaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/602,177

(22) Filed: Jun. 22, 2000

(51) Int. Cl.[7] ..... A01H 5/00
(52) U.S. Cl. ..... Plt./250
(58) Field of Search ..... Plt./250

(56) References Cited

U.S. PATENT DOCUMENTS

PP11,038 P * 8/1999 Benarcik, Jr. ..... Plt./250

* cited by examiner

*Primary Examiner*—Kent L. Bell
(74) *Attorney, Agent, or Firm*—Christie, Parker & Hale, LLP

(57) ABSTRACT

A new plant variety of *Hydrangea anomala* subspecies petiolaris having new shoots and foliage that emerge white, cream, pale yellow to pink with pink stems. Foliage goes through a phase in which leaves are flecked/dotted cream to pale yellow sometimes with margin pale yellow in an irregular variegated pattern. Mature foliage is viridescent with leaves becoming green.

3 Drawing Sheets

BACKGROUND OF THE INVENTION

The present invention relates to a new and distinct variety of *Hydrangea anomala* D. Don. subspecies *petiolaris* (Sieb. & Zucc.) McClint., and was discovered as a branch sport in a controlled planting of an unnamed, unpatented *Hydrangea anomala* subspecies *petiolaris* plant in Kuga-Cho, Kuga-Gun, Yamaguchi Prefecture, Japan, by Mr. Toshiro Shimuzu. The varietal denomination of the new variety is 'Kuga variegated'.

The genus Hydrangea is included in the family Saxifragaceae which comprises about 80 genera and 1,200 species of herbs, shrubs, small trees, woody climbers mostly temperate in origin. Recent taxonomical treatments sometimes isolate Hydrangea in a new family, Hydrangeaaceae. Hydrangea comprises approximately 23 species of deciduous or evergreen shrubs and vines originating in North America, South America and East Asia, many of which possess desirable ornamental characteristics.

*Hydrangea anomala* subspecies *petiolaris* is widespread and common throughout Japan and some locations within Korea. It generally has opposite, oval to rounded leaves 5 to 10 cm long and 3 to 8 cm wide. Leaves are acute or acuminate to apex, cordate or round at the base. Leaf margins are serrate, glabrous on surface. The plant is deciduous. Foliage color is dark green on the top surface, and pale green on the underside, depending on light. The species *Hydrangea anomala* differs from *H. anomala* subspecies *petiolaris* by having smaller leaves, corymbs are smaller and stamen count is 9 to 15. All *Hydrangea anomala* sub. *petiolaris* have a juvenile and adult phase of growth. Plants in the juvenile growth phase have smaller leaves and do not flower. Some foliar characteristics change as the plant enters the adult phase as well and begins to flower.

Inflorescenses of *Hydrangea anomala* subsp. *petiolaris* bloom in June to July, are 15 to 25 cm wide, with sepals in groups of 3 to 5 on the outer florets. The inner florets are fertile, and slightly fragrant with 15 to 22 stamens.

SUMMARY OF THE INVENTION

The new variety has new shoots and foliage that emerge white, cream, pale yellow to pink, with pink stems. Foliage goes through a phase in which leaves are flecked/dotted cream to pale yellow sometimes with margin pale yellow in an irregular variegated pattern. Mature foliage is viridescent with leaves becoming green. Asexual reproduction of the new variety by stem cuttings performed in Yamaguchi Prefecture, Japan; Lewisberry, Pa.; and Vacaville, Calif.; have confirmed that the distinctive characteristics of the new variety are stable and transmitted to suceeding generations.

COMPARISON WITH PARENT

The new variety differs from its parent in coloration of new shoots and foliage that emerge white, cream, pale yellow to pink, with pink stems, becoming flecked/dotted cream to pale yellow sometimes with pale yellow margins in an irregular variegated pattern.

BRIEF DESCRIPTION OF ILLUSTRATIONS

The accompanying illustrations show specimens of the new cultivar in a photo illustration as true to color as is reasonably possible to make in an illustration of this character.

DESCRIPTION OF THE NEW VARIETY

Figure 1:
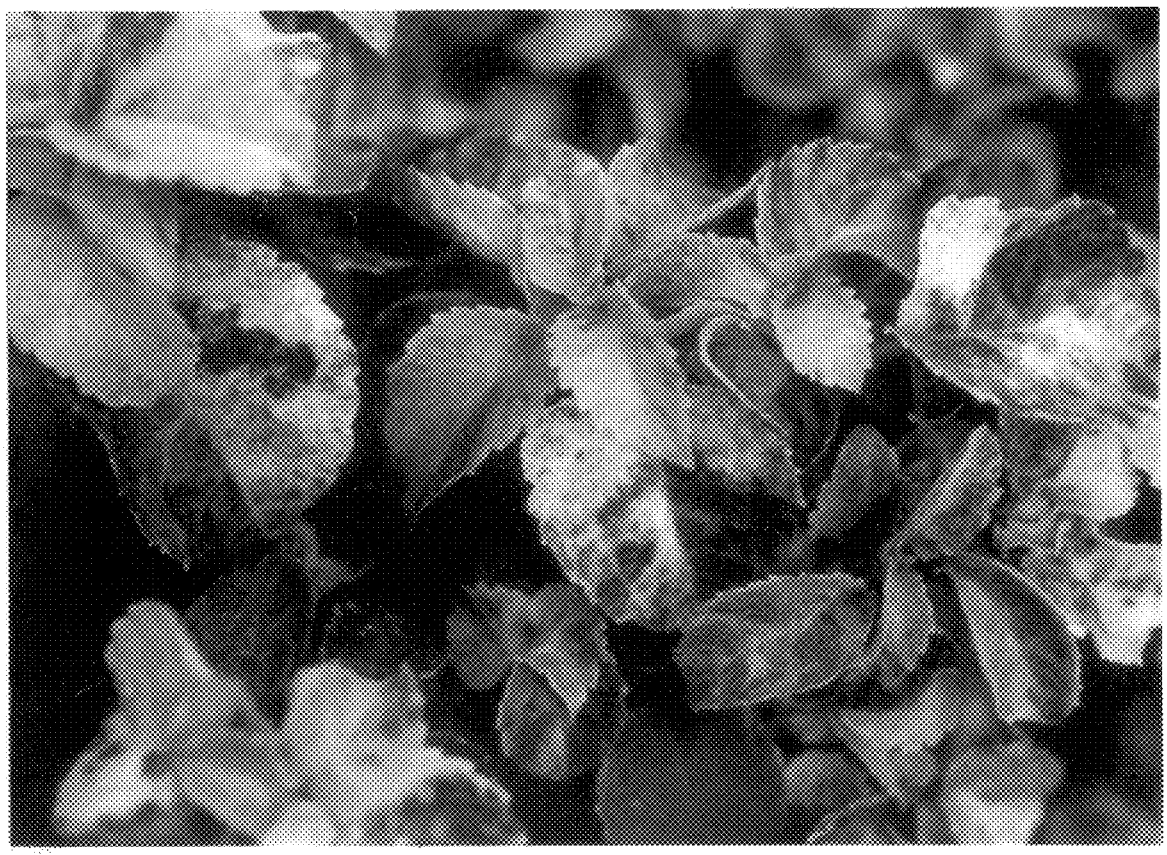
FIG. 1 shows the new foliage as well as the secondary foliage prior to maturation.
Figure 2:
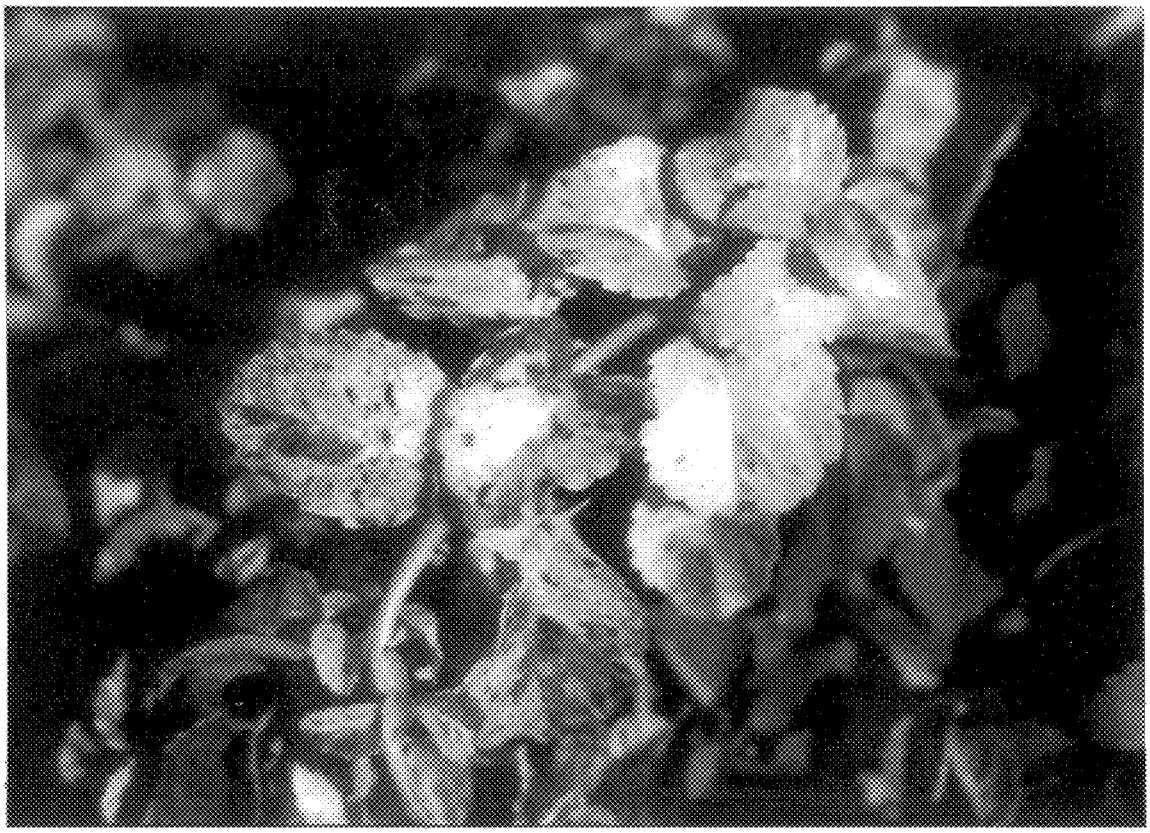
FIG. 2 illustrates the new growth as well as the newly emerged growth.
Figure 3:
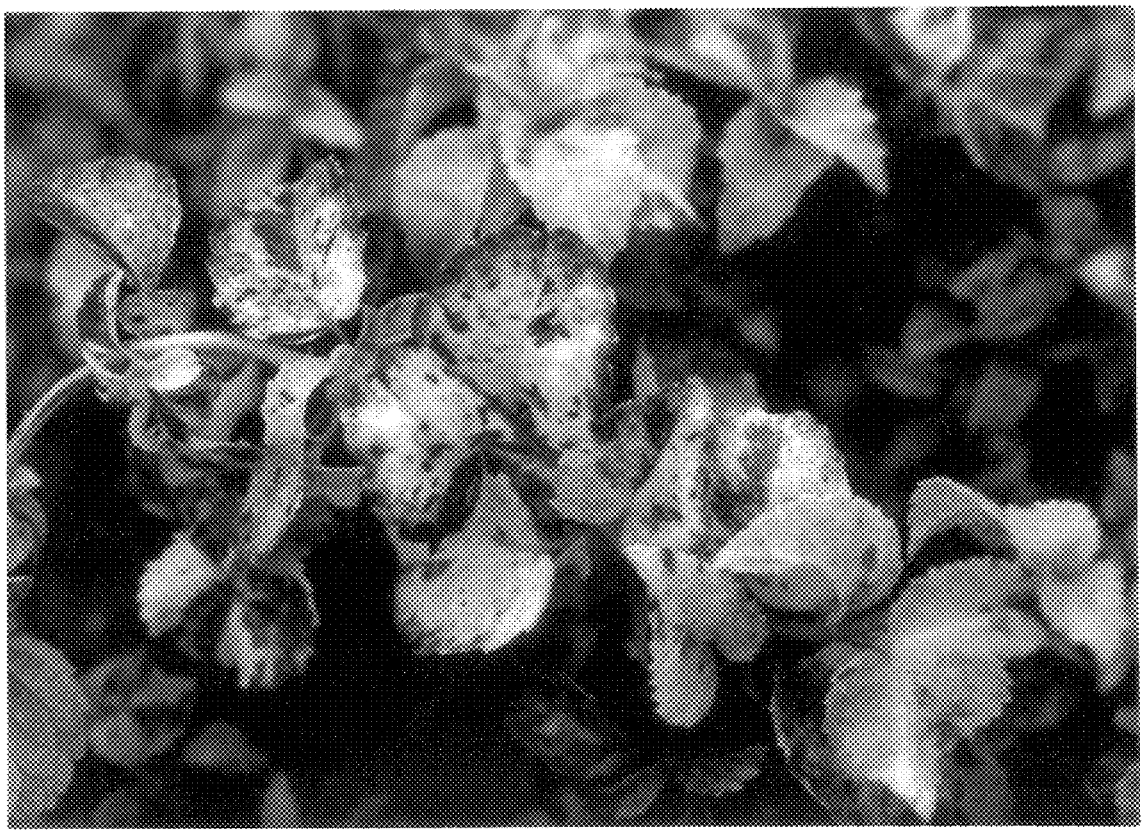
FIG. 3 is an illustration of the secondary foliage with the distinct flecked/dotted cream to pale yellow variegation.

'Kuga Variegated' has not been observed under all possible environmental, cultural, and light conditions. The following observations and descriptions are of 5-year-old plants grown in 10-gallon containers at Lewisberry, Pa., and Vacaville, Calif. In the description, color references are to The Royal Horticultural Society Colour Chart (1995) and terminology used in the color descriptions herein refers to plate numbers in this color chart. Phenotypic expression may vary with light intensity, cultural, and environmental conditions.

CLASSIFICATION

Botanical: *Hydrangea anomala* D. Don. subspecies *petiolaris* (Sieb. & Zucc.) McClint. 'Kuga Variegated'.

Parentage: Branch sport of a *Hydrangea anomala* subspecies *petiolaris* plant (unnamed, unpatented).

Propagation: By vegetative cuttings.

Plant:

*Size.*—Mature plant can climb and spread to about 16 meters at maturity.

*Habit.*—A clinging vine climbing with root like holdfasts.

*Leaves.*—Opposite, simple, ovate to ovate oval, about 5 to 10 cm long, 3 to 8 cm wide; acute or acuminate at apex, cordate at base.

*Left margin.*—Serrate.

*Stems.*—Hirsute on new growth.

*Internodes.*—4 cm in length.

COLOR OF LEAVES IN THREE DIFFERENT GROWTH PHASES

New growth:

*Variegation leaf top.*—Near 41B.

*Variegation leaf underside.*—Near 41B.

*Stems.*—Near 47B.

Secondary growth:

*Variegation leaf top.*—Near 2B to 2C.

*Variegation leaf bottom.*—Near 2B to 2D.

*Mottled variegation region.*—Near 147A.

Mature growth:

*Top of leaf.*—Near 147A.

*Leaf bottom.*—Near 147C.

*Leaf size.*—Average about 5 to 10 cm long and 3 to 8 cm wide.

*Shape.*—Ovate to nearly ovate oval.

*Texture and substance.*—Firm and glabrous above and below.

*Leaf apex.*—Acute to ovate oval.

*Leaf base.*—Cordate.

*Petioles.*—About 5 mm long; near Red Group 47B.

*Hardiness.*—USDA Zone 4 (−30 F. to −20 F.).

*Pest/diseases.*—No pest or disease problems noted.

Inflorescence:

*Bloom period.*—Early to mid-summer.

*Lastingness of individual bloom.*—To 3 weeks.

*Inflorescence form.*—Flat corymbs, 3 to 5 corymbs per plant, outer florets sterile, inner florets fertile.

*Inflorescence size.*—About 15 to 25 cm wide.

*Color.*—White.

*Fragrance.*—Sweet.

*Outer florets.*—Grouping of 3 to 5 sepals, sterile, about 5 to 10 cm wide.

*Number of sepals per floret.*—12 to 18.

*Sepal length.*—Approximately 2.5 cm.

*Sepal width.*—Approximately 2.5 cm.

*Sepal shape.*—Round.

*Sepal margin.*—Entire.

*Sepal color.*—Top near White Group 155A; bottom near White Group 155A.

*Inner florets.*—Fertile.

*Stamens.*—About 15 to 20.

*Pistils.*—1.

*Fruit.*—Capsule, dehiscent.

I claim:

1. A new plant of *Hydrangea anomala* subspecies *petiolaris* substantially as shown and described.

* * * * *